US008313424B2

(12) United States Patent
Gabrielidis

(10) Patent No.: US 8,313,424 B2
(45) Date of Patent: Nov. 20, 2012

(54) SEX TOY

(76) Inventor: Pericles Gabrielidis, Sylmar, CA (US)

(*) Notice: Subject to any disclaimer, the term of this patent is extended or adjusted under 35 U.S.C. 154(b) by 455 days.

(21) Appl. No.: 12/244,157

(22) Filed: Oct. 2, 2008

(65) Prior Publication Data

US 2010/0087703 A1 Apr. 8, 2010

(51) Int. Cl.
*A61F 5/00* (2006.01)

(52) U.S. Cl. .......................................................... 600/38

(58) Field of Classification Search .............. 600/38-41; 128/897, 898

See application file for complete search history.

(56) References Cited

U.S. PATENT DOCUMENTS

| | | | | | |
|---|---|---|---|---|---|
| 2,059,531 | A | * | 11/1936 | Long | 137/515.5 |
| 3,847,336 | A | * | 11/1974 | Morris et al. | 248/291.1 |
| 4,063,701 | A | * | 12/1977 | Wray | 248/292.14 |
| 5,690,604 | A | * | 11/1997 | Barnett | 600/38 |
| 5,851,175 | A | * | 12/1998 | Nickell | 600/38 |
| 6,179,795 | B1 | | 1/2001 | Garza | |
| 6,540,667 | B2 | * | 4/2003 | Hickman | 600/38 |
| 6,899,671 | B1 | | 5/2005 | Fontenot | |
| 6,991,599 | B2 | * | 1/2006 | Hudson | 600/38 |
| 7,077,817 | B2 | | 7/2006 | Young et al. | |
| 7,267,646 | B2 | | 9/2007 | Tucker | |
| 2006/0047181 | A1 | * | 3/2006 | Hsu | 600/38 |

* cited by examiner

*Primary Examiner* — Samuel Gilbert

(74) *Attorney, Agent, or Firm* — Kelly & Kelley, LLP

(57) ABSTRACT

The sex toy of the present invention has a handle connected to one end of an elongated shaft and a dildo pivotally attached to a second end of the elongated shaft. The shaft includes an arcuate section proximate to the second end. The pivotal attachment of the dildo to the shaft facilitates vaginal and anal insertion of the dildo by a user. The configuration of the sex toy is easy to use while increasing the level of stimulation.

18 Claims, 5 Drawing Sheets

SEX TOY

BACKGROUND OF THE INVENTION

The present invention relates generally to sex toys. More particularly, the present invention relates to a sex toy that may be easily moved in a lateral sliding action with minimal rotation or lateral movement of the grips.

Throughout history, humans have sought sexual gratification by artificial means. Such artificial means have included orifices to simulate male organs. Other artificial means have included phallic devices to facilitate vaginal or anal stimulation. The present device is directed to the latter.

Typical phallic devices or dildos are hand-held and require that a user either have a partner or contort their body in unusual positions to achieve proper and repeated insertion. Many have attempted to design an improved sex toy, both manual and mechanical, that facilitates insertion of a dildo. Such mechanical devices can become large and cumbersome which could interfere with a person's desire to be discrete or private when using such a device. Further, manual devices can likewise become large and awkward to use.

Accordingly, there is a need for a sex toy that is compact in size and easy to manipulate. In addition, there is a need for a sex toy that can be easily moved with minimal strain on the hands, wrists and forearms. The present invention fulfills these needs and provides other related advantages.

SUMMARY OF THE INVENTION

The present invention is directed to a sex toy comprising an elongate shaft having a first end and an opposite second end, a handlebar generally perpendicularly connected to the first end of the shaft and a dildo pivotally attached to the second end of the shaft. The handlebar terminates proximate to the first end of the shaft and includes hand grips disposed proximate and perpendicular to the first end of the shaft. The shaft includes an arcuate section forming an obtuse angle, which extends and terminates proximate to the second end of the shaft.

The dildo pivots relative to the shaft in two orthogonal directions. In addition, the dildo is generally shaped like a penis and is configured for vaginal or anal penetration. The dildo may include a vibrator and/or internally rotating beads.

A bracket is fixed to one of the second end of the shaft or the dildo and a connecting flange is fixed to the other one of the second end of the shaft or the dildo. A pin connects the flange to the bracket in a manner that permits pivoting movement of the dildo relative to the second end of the shaft.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

Figure 1:
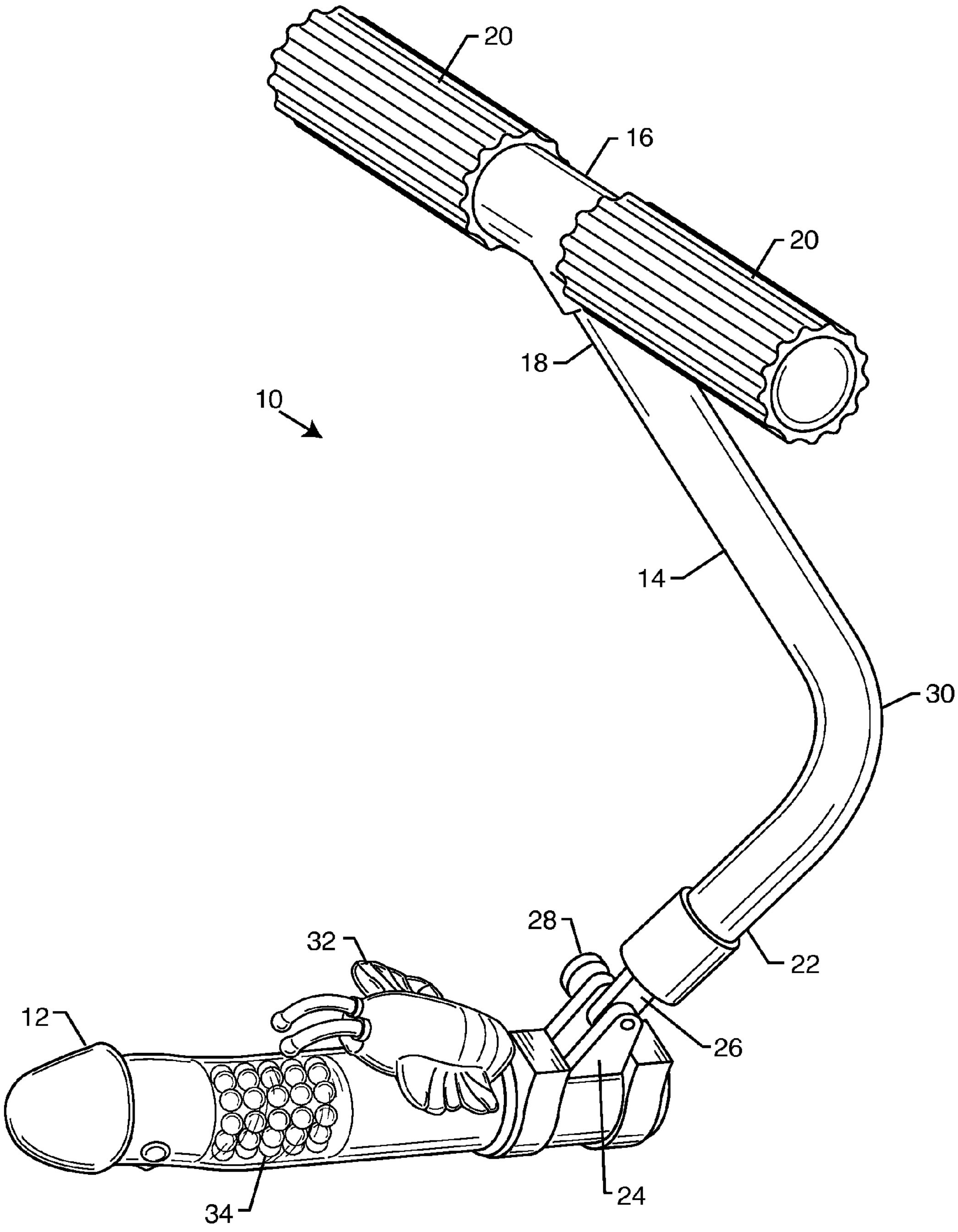
FIG. 1 is an orthogonal view of a preferred embodiment of the present invention.
Figure 2:
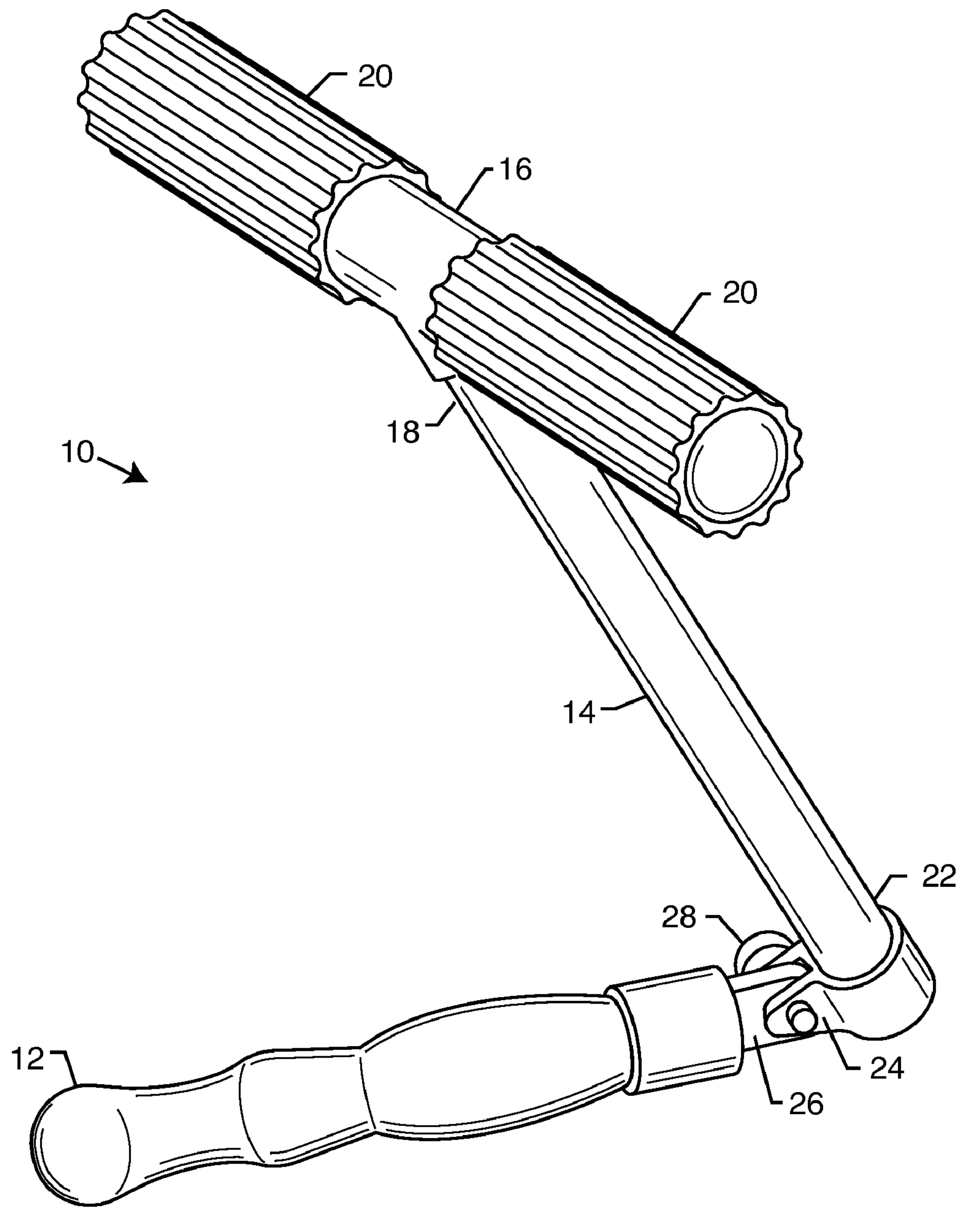
FIG. 2 is an orthogonal view of another preferred embodiment of the present invention.
Figure 3:
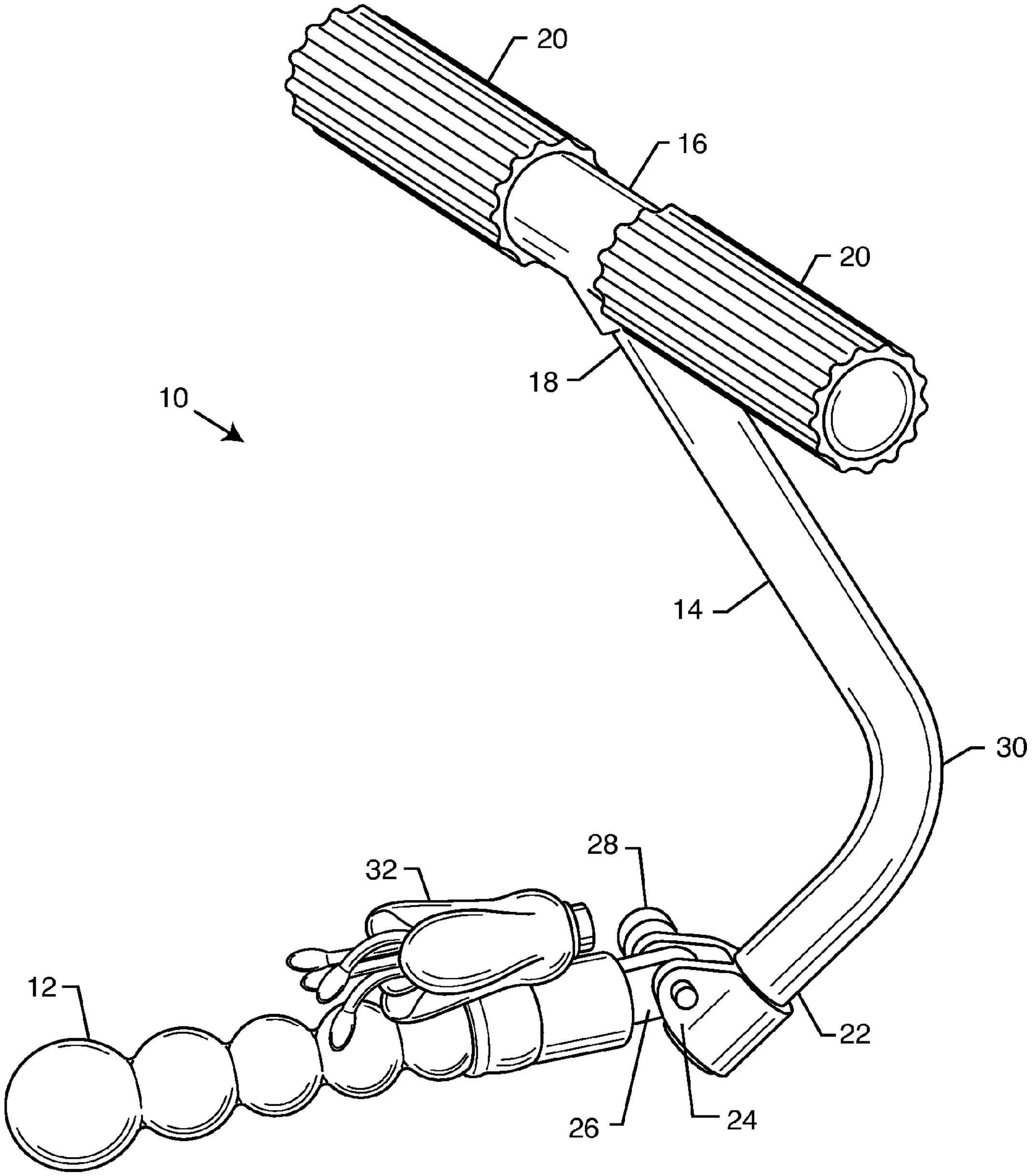
FIG. 3 is an orthogonal view of another preferred embodiment of the present invention.

As shown in FIGS. 1-3, for purposes of illustration, the present invention is directed to a sex toy generally referred to by reference numeral 10. Different embodiments of the sex toy 10 will be described below. Throughout the description of each embodiment, the same reference numerals will be used to refer to similar components, including the dildo 12.

As depicted in FIGS. 1-3, every embodiment of the inventive sex toy 10 includes a dildo 12, an elongated shaft 14 and a handle 16. The shaft 14 and handle 16 are preferably made from metal or a hard rigid plastic. The dildo 12 is preferably made from any material commonly used for such devices which will be comfortable for the user. The handle 16 is generally perpendicularly connected to a first end 18 of the shaft 14 and terminates proximate thereto. The handle 16 includes hand grips 20 proximate and perpendicular to the first end 18 of the shaft 14, which permit a user to comfortably and reliably grasp the sex toy 10. The hand grips 20 are preferably made from a soft rubber or plastic which provides a comfortable surface for grasping.

The dildo 12 is pivotally attached to a second end 22 of the shaft 14. This pivotal attachment may be achieved by a bracket 24 connected to a flange 26 by a pin 28. As illustrated in FIG. 1, the bracket 24 may be fixed to the dildo 12 and the flange 26 may be fixed to the second end 22 of the shaft 14. Alternatively, as shown in FIGS. 2 and 3, the bracket 24 may be fixed to the second end 22 of the shaft 14 and the flange 26 fixed to the dildo 12. In either configuration, the dildo 12 is generally pivotable in line with the shaft 14.

In either configuration the connection between the second end 22 of the shaft 14 and either the bracket 24 or the flange 26 may permit rotation of the shaft while the dildo 12 remains stationary. Such rotation allows the dildo 12 to pivot relative to the shaft 14 in two orthogonal directions The shaft 14 preferably includes an arcuate section 30 between the first end 18 and second end 22. The arcuate section 30 forms an obtuse angle that extends and terminates proximate to the second end 22 of the shaft 14. This arcuate section is important to allow the sex toy 10 to clear a user's pubic bone when using the device. The arcuate section 30 also makes it easier for a person to use the sex toy 10 by relieving stress and strain on the hands, wrist and forearms.

The dildo 12 may be a simple phallus for insertion into an opening. (FIG. 2) The dildo 12 may also include a number of attachments such as an external vibrator 32 and/or internally rotating beads 34. (FIGS. 1 and 3).

The sex toy 10 of the present invention allows for use in any position, i.e., from the front, from the rear, standing or lying down. In addition, the sex toy 10, while configured for solo use, may be used with a partner as well. The dildo 12 may be inserted in a vagina or an anus providing for stimulation of either.

Figure 4:
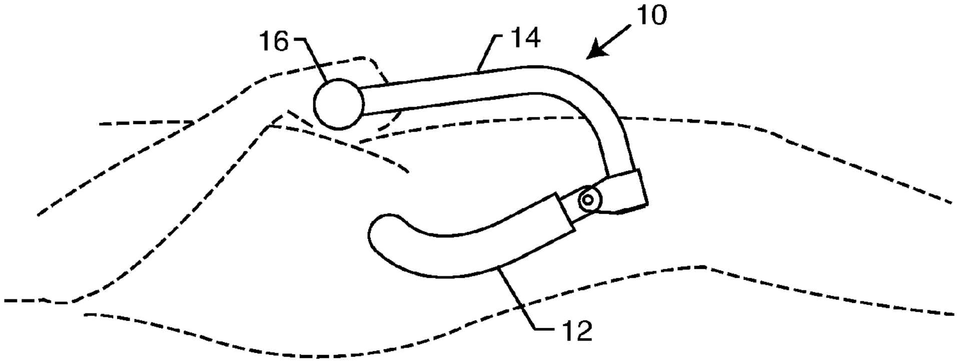
FIG. 4 is an illustration depicting vaginal insertion of the sex toy of the present invention.
Figure 5:
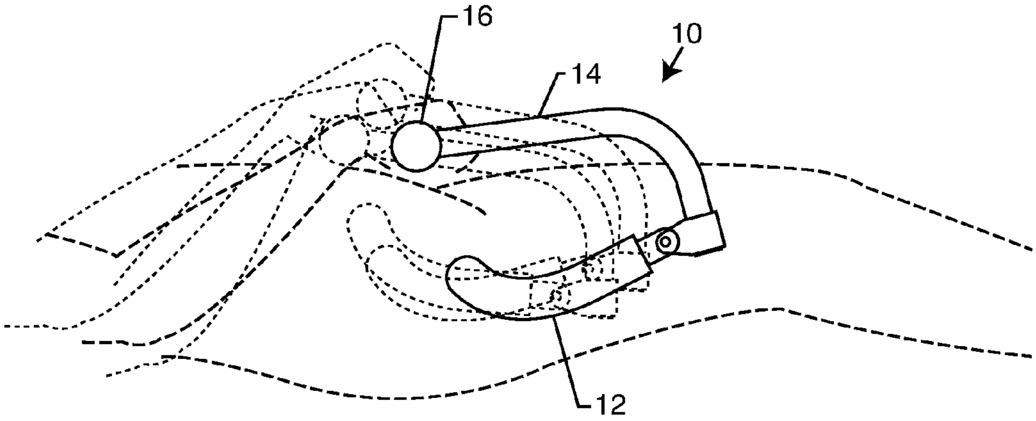
FIG. 5 is an illustration depicting movement of the sex toy of the present invention during vaginal insertion.

FIGS. 4 and 5 illustrate use of the sex toy 10 in a prone position. As shown in FIG. 4, a woman begins by inserting the dildo 12 into her vagina (not shown). As shown in FIG. 5, movement of the handle 16 rotationally and back and forth along the body results in movement of the dildo 12 into and out of the vagina. The pivoting attachment of the dildo 12 to the second end 22 of the shaft 14 provides for greater comfort and less awkwardness when moving the handle 16.

Figure 6:
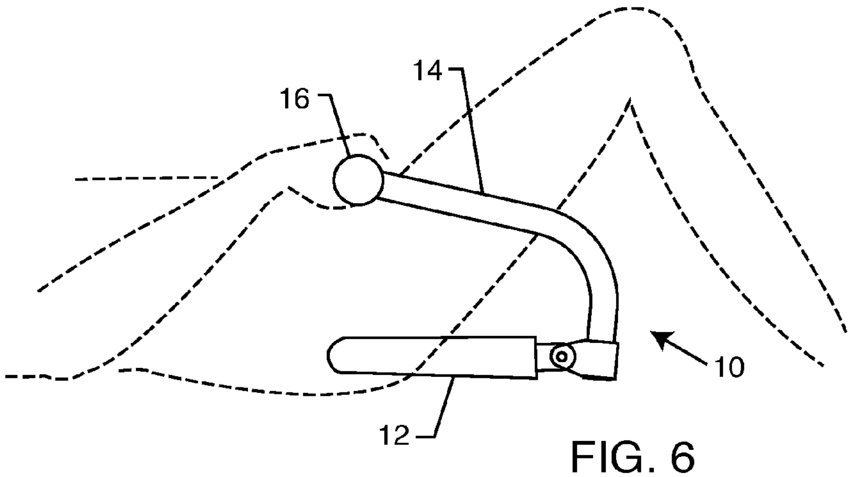
FIG. 6 is an illustration depicting anal insertion of the sex toy of the present invention.

FIG. 6 illustrates anal insertion of the dildo 12 by a man or a woman in a prone position. As with vaginal insertion, one may stimulate the anus by movement of the handle 16 rotationally and back and forth along the body. Such movement of the handle 16 will cause the dildo 12 to move in and out of the anus. In a prone position it is preferable that a user rest his or her arms on their abdomen. Resting ones arms on the abdomen helps to relieve stress and strain in the hands, wrist and forearms and provide greater leverage for movement of the dildo 12.

Figure 7:
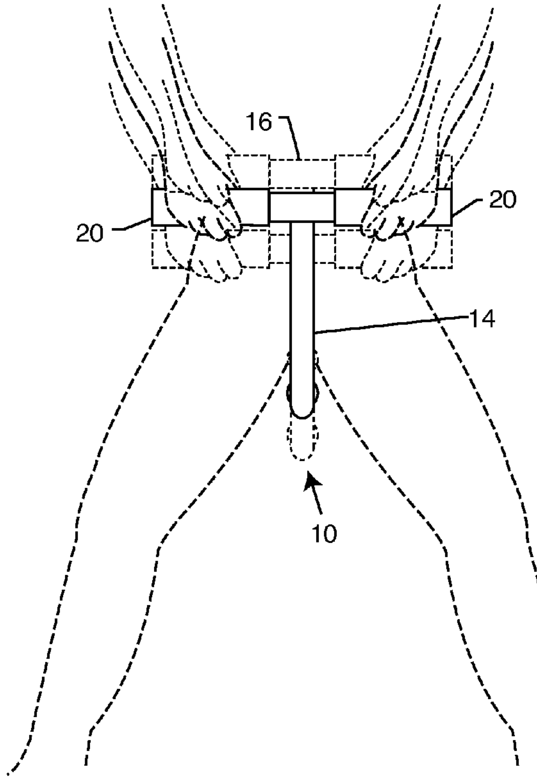
FIG. 7 is an illustration depicting sliding movement of the sex toy of the present invention during insertion.
Figure 8:
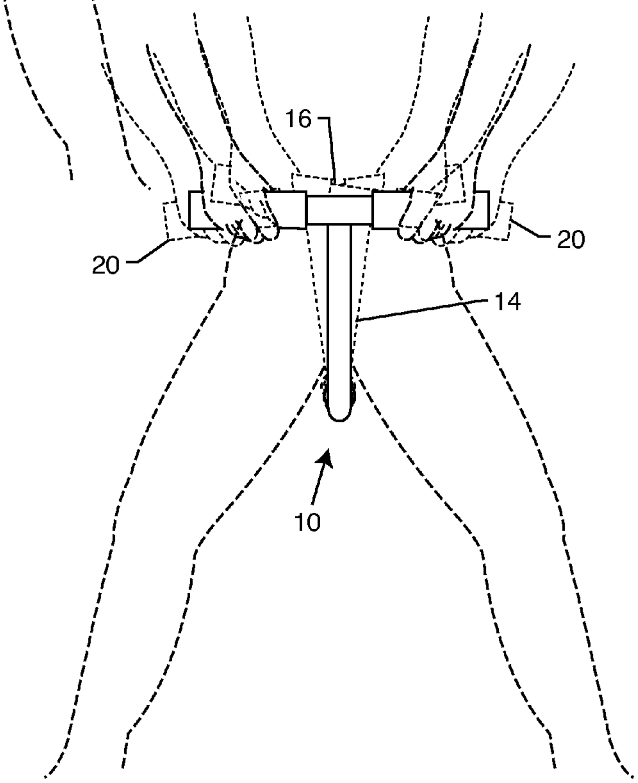
FIG. 8 is an illustration depicting lateral pivoting movement of the sex toy of the present invention during insertion.

FIGS. 7 and 8 illustrate two kinds of movement of the sex toy 10 of the present invention. In either illustration, the user may be standing or lying in a prone position. As shown in FIG. 7, movement of ones hands along the body will result in a thrusting movement of the dildo 12 into and out of the vaginal or anal opening. As shown in FIG. 8, side-to-side movement of the hands will result in side-to-side movement of the shaft 14.

Where the shaft 14 is pivotally connected to the bracket 24 or flange 26, such side-to-side movement will change the angle of the shaft 14 with respect to the dildo 12. With the changed angle, subsequent in and out movement of the dildo 12 will cause a different portion of the vaginal or anal opening to receive pressure and thus greater stimulation. Where the shaft 14 does not pivot with respect to the bracket 24 or flange 26, side-to-side movement of the handle will achieve increased pressure of the dildo 12 against the side walls of the vaginal or anal opening with or without subsequent thrusting movement.

A user may combine the up and down movement with the side-to-side movement of the handle 16 to achieve a combined circular motion of the dildo 12 in the vaginal or anal opening. In addition, a user may turn the sex toy 10 around with the handle 16 and his or her hands behind the body to achieve different angles of insertion and different sensations.

Although several embodiments have been described in detail for purposes of illustration, various modifications may be made without departing from the scope and spirit of the invention. Accordingly, the invention is not to be limited, except as by the appended claims.

What is claimed is:

1. A sex toy, comprising:

an elongate shaft having a first end and an opposite second end wherein the shaft has a total angular displacement forming an obtuse angle;

a handlebar generally perpendicularly connected to the first end of the shaft wherein the handlebar terminates proximate to the first end of the shaft and includes hand grips disposed proximate and perpendicular to the first end of the shaft;

a dildo attached to the second end of the shaft; and means for pivoting the dildo relative to the shaft.

2. The sex toy of claim 1, wherein the total angular displacement begins and ends proximate the second end of the shaft.

3. The sex toy of claim 1, wherein the means for pivoting the dildo relative to the shaft permits pivoting in two orthogonal directions.

4. The sex toy of claim 1, wherein the dildo includes a vibrator.

5. The sex toy of claim 1, wherein the dildo includes internally rotating beads.

6. The sex toy of claim 1, wherein the dildo is generally shaped like a penis.

7. The sex toy of claim 1, wherein the dildo is configured for vaginal or anal penetration.

8. The sex toy of claim 1, wherein the means for pivoting comprises a bracket, a connecting flange, and a pin; the bracket fixed to one of the second end of the shaft or the dildo, the connecting flange fixed to the other one of the second end of the shaft or the dildo, and the pin for connecting the flange to the bracket in a manner permitting pivotal movement of the dildo relative to the shaft.

9. The sex toy of claim 1, wherein the ends of the handle bar terminate in outwardly opposite directions from the shaft.

10. A sex toy, comprising:

an elongate shaft having a first end and an opposite second end;

a handlebar generally perpendicularly connected to the first end of the shaft, wherein the handlebar includes handgrips disposed proximate to the first end of the shaft; and means for attaching a dildo to the second end of the shaft, wherein means for attaching is configured such that the shaft rotates while the dildo remains stationary and the dildo pivots relative to the shaft.

11. The sex toy of claim 10, wherein the shaft has a total angular displacement forming an obtuse angle.

12. The sex toy of claim 11, wherein the total angular displacement begins and ends proximate the second end of the shaft.

13. The sex toy of claim 10, wherein the means for attaching the dildo to the second end of the shaft permits pivoting in two orthogonal directions.

14. The sex toy of claim 10, wherein the dildo includes a vibrator.

15. The sex toy of claim 10, wherein the dildo includes internally rotating beads.

16. The sex toy of claim 10, wherein the dildo is generally shaped like a penis.

17. The sex toy of claim 10, wherein the dildo is configured for vaginal or anal penetration.

18. The sex toy of claim 10, wherein the means for attaching comprises a bracket, a connecting flange, and a pin; the bracket fixed to one of the second end of the shaft or the dildo, the connecting flange fixed to the other one of the second end of the shaft or the dildo, the bracket and/or connecting flange permitting rotational movement of the dildo relative to the shaft, and the pin for connecting the flange to the bracket in a manner permitting pivotal movement of the dildo relative to the shaft.

* * * * *